(12) United States Patent
Miao et al.

(10) Patent No.: US 8,442,353 B2
(45) Date of Patent: May 14, 2013

(54) INCORPORATION OF MATHEMATICAL CONSTRAINTS IN METHODS FOR DOSE REDUCTION AND IMAGE ENHANCEMENT IN TOMOGRAPHY

(75) Inventors: Jianwei Miao, Manhattan Beach, CA (US); Benjamin P. Fahimian, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 298 days.

(21) Appl. No.: 12/978,093

(22) Filed: Dec. 23, 2010

(65) Prior Publication Data

US 2011/0164799 A1 Jul. 7, 2011

Related U.S. Application Data

(63) Continuation of application No. PCT/US2009/051290, filed on Jul. 21, 2009, and a continuation-in-part of application No. 12/840,065, filed on Jul. 20, 2010, which is a continuation of application No. PCT/US2009/032733, filed on Jan. 30, 2009, and a continuation-in-part of application No. 12/363,079, filed on Jan. 30, 2009, now Pat. No. 8,270,760, which is a continuation of application No. PCT/US2007/075220, filed on Aug. 3, 2007.

(60) Provisional application No. 61/083,105, filed on Jul. 23, 2008, provisional application No. 61/024,762, filed on Jan. 30, 2008, provisional application No. 60/835,552, filed on Aug. 3, 2006.

(51) Int. Cl.
*G06K 9/36* (2006.01)

(52) U.S. Cl.
USPC ........... 382/280; 382/274; 382/275; 382/282; 358/3.26; 358/3.27; 358/463

(58) Field of Classification Search .................. 382/260, 382/274, 275, 280, 282; 358/3.26, 3.27, 358/463
See application file for complete search history.

(56) References Cited

U.S. PATENT DOCUMENTS 4,506,327 A 3/1985 Tam
4,616,318 A 10/1986 Crawford
(Continued)

FOREIGN PATENT DOCUMENTS

WO 2007026234 A1 3/2007
WO 2008017076 A2 2/2008

OTHER PUBLICATIONS

Mao, Yu et al.—"Development and Optimization of Regularized Tomographic Reconstruction Algorithms Using Equally-Sloped Tomography"—IEEE Transactions on Image Processing, vol. 19, No. 5, May 2010, pp. 1259-1268.

(Continued)

*Primary Examiner* — Yosef Kassa
(74) *Attorney, Agent, or Firm* — John P. O'Banion

(57) ABSTRACT

A system and method for creating a three dimensional cross sectional image of an object by the reconstruction of its projections that have been iteratively refined through mathematical transformations and modifications in object space and Fourier space is disclosed. A primary benefit of the method is radiation dose reduction since the invention can produce an image of a desired quality with a fewer number projections than seen with conventional methods.

20 Claims, 7 Drawing Sheets

U.S. PATENT DOCUMENTS

| | | | |
|---|---|---|---|
| 4,752,879 | A | 6/1988 | Brunnett |
| 4,888,693 | A | 12/1989 | Tam |
| 5,751,243 | A | 5/1998 | Turpin |
| 5,761,267 | A | 6/1998 | Besson |
| 5,937,102 | A | 8/1999 | Jin |
| 6,304,317 | B1 | 10/2001 | Taniguchi et al. |
| 6,366,638 | B1 | 4/2002 | Hsieh |
| 6,744,848 | B2 | 6/2004 | Stanton et al. |
| 6,862,337 | B2 | 3/2005 | Claus et al. |
| 6,873,744 | B2 | 3/2005 | Ottesen |
| 6,920,240 | B2 | 7/2005 | Rodet et al. |
| 7,076,091 | B2 | 7/2006 | Rosenfeld |
| 7,209,535 | B2 | 4/2007 | Chen et al. |
| 7,218,959 | B2 * | 5/2007 | Alfano et al. ............ 600/476 |
| 7,245,124 | B2 * | 7/2007 | Shu et al. ............... 324/307 |
| 7,298,143 | B2 * | 11/2007 | Jaermann et al. ........ 324/307 |
| 7,315,636 | B2 | 1/2008 | Kuduvalli |
| 7,379,575 | B2 * | 5/2008 | Ruhrnschopf ............ 382/128 |
| 7,436,507 | B2 | 10/2008 | Moribe |
| 7,439,739 | B2 | 10/2008 | Beatty |
| 7,467,046 | B2 * | 12/2008 | Taylor et al. ............. 702/19 |
| 7,471,768 | B2 * | 12/2008 | Curtis et al. ............. 378/115 |
| 7,787,588 | B1 * | 8/2010 | Yun et al. ................ 378/43 |
| 7,821,266 | B2 * | 10/2010 | Feiweier ................. 324/309 |
| 7,957,609 | B2 * | 6/2011 | Lu et al. ................. 382/280 |
| 2003/0095596 | A1 | 5/2003 | Shimizu |
| 2003/0198403 | A1 | 10/2003 | Ottesen |
| 2004/0076257 | A1 | 4/2004 | McDaniel |
| 2004/0215072 | A1 | 10/2004 | Zhu |
| 2004/0264634 | A1 | 12/2004 | Claus et al. |
| 2005/0047636 | A1 | 3/2005 | Gines et al. |
| 2007/0003122 | A1 | 1/2007 | Sirohey et al. |
| 2007/0053477 | A1 | 3/2007 | Ning |
| 2007/0160304 | A1 | 7/2007 | Berkner |
| 2007/0232890 | A1 | 10/2007 | Hirota |
| 2008/0273651 | A1 | 11/2008 | Boas |
| 2009/0221920 | A1 | 9/2009 | Boppart |
| 2009/0232377 | A1 | 9/2009 | Miao et al. |
| 2009/0262118 | A1 | 10/2009 | Arikan et al. |
| 2010/0284596 | A1 | 11/2010 | Miao et al. |
| 2011/0007980 | A1 | 1/2011 | Fahimian et al. |
| 2011/0044546 | A1 | 2/2011 | Pan et al. |

OTHER PUBLICATIONS

State Intellectual Property Office of P.R. China, The Notification of the Second Office Action (translation) issued Jun. 15, 2011, related Chinese Patent Application No. 200780028681.0, counterpart to PCT/US2008/075220, with claims examined, pp. 1-16.

Korean Intellectual Property Office (KIPO), International Search Report and Written Opinion dated Dec. 16, 2010, including claims searched, related PCT Application No. PCT/US2012/033162, pp. 1-12.

European Patent Office, Extended European Search Report issued on Oct. 31, 2011, related EPO Patent Application No. 07840699.8, counterpart to PCT/US2007/075220, with claims searched, pp. 1-14.

Delaney, A.H. et al.—"A Fast and Accurate Fourier Algorithm for Iterative Parallel-Beam Tomography"—IEEE Trans. on Image Processing, vol. 5, No. 5, May 1996, pp. 740-753.

Ye, J. et al.—"A Self-Referencing Level-Set Method for Image Reconstruction from Sparse Fourier Samples"—Int. Jour. of Computer Vision, vol. 50, No. 3, 2002, pp. 253-270.

Erlandsson, K. et al.—"A New 3D Backprojection and Filtering Method for PET Using All Detected Events"—IEEE Trans. on Nuclear Science, vol. 45, No. 3, Jun. 1998, pp. 1183-1188.

Olson, T.—"Limited Angle Tomography Via Multiresolution Analysis and Oversampling"—Proc. of the IEEE Time-Frequency and Time-Scale Analysis, Oct. 4, 1992, pp. 215-218.

Australian Government, IP Australia, Examiner's First Report dated Nov. 30, 2011, related AU Application No. 2007281076, counterpart to PCT/US2007/075220, with claims examined, pp. 1-23.

WIPO, related PCT Application No. PCT/US2009/032733, International Publication No. WO 2009/097580 dated Aug. 6, 2009, including international search report and written opinion issued on Sep. 1, 2009, pp. 1-39.

WIPO, counterpart PCT Application No. PCT/US2009/051290, International Publication No. WO 2010/011676 dated Jan. 28, 2010, including international search report and written opinion issued on Feb. 18, 2010, pp. 1-46.

The Notification of the First Office Action, State Intellectual Property Office of P.R. China, Patent Application No. 200780028681.0, issued Jun. 9, 2010, with claims, counterpart to PCT/US2009/32733 claiming priority to U.S. Appl. No. 61/024,762, pp. 1-18.

Miao, J. et al.—"Three-Dimensional GaN-Ga2O3 Core Shell Structure Revealed by X-Ray Diffraction Microscopy"—Phys. Rev. Lett. 97, 2006, pp. 215503-1-215503-4.

Averbuch, A. et al.—"Fast and accurate Polar Fourier transform"—App. Comput. Harmon. Anal. 21, 2006, pp. 145-167.

WIPO, related PCT Application No. PCT/US2007/075220, International Publication No. WO 2008/017076 dated Feb. 7, 2008, including international search report and written opinion issued on Apr. 10, 2008, pp. 1-66.

Tam, K.G., Eberhard, J.W., Mitchell, K.W., "IEEE Transactions on Nuclear Science," vol. 37, No. 3, Jun. 1990, pp. 1-10.

Miao, J., Forster, F., Levi, O., "Equally sloped tomography with oversampling reconstruction." Physical Review B 72, No. 5 (2005), pp. 1-4.

Ozaktas, H.M., Arikan, O.M., Kutay, A., and Bozdagt, G., "Digital computation of the fractional Fourier transform" Signal Processing, IEEE Transactions on 44, No. 9, (1996): 2141-2150, pp. 1-10.

Yin, W., Osher, S., Goldfarb, D., and Darbon, J., "Bregman iterative algorithms for l1-minimization with applications to compressed sensing" SIAM Journal on Image Sciences 1, No. 1 (2008): 143-168, pp. 1-26.

United States Patent and Trademark Office (USPTO), Office Action issued on Nov. 9, 2012 (pp. 1-40), including claims examined (pp. 41-46) for U.S. Appl. No. 12/771,449, pp. 1-46.

European Patent Office, European Extended Search Report, EPO Appln. No. 09800891.5, with claims searched, Sep. 21, 2012, pp. 1-9.

Lee et al., "Radiation dose reduction and image enhancement in biological imaging through equally-sloped tomography", Journal of Structural Biology, vol. 164, Aug. 15, 2008, pp. 221-227.

* cited by examiner

INCORPORATION OF MATHEMATICAL CONSTRAINTS IN METHODS FOR DOSE REDUCTION AND IMAGE ENHANCEMENT IN TOMOGRAPHY

CROSS-REFERENCE TO RELATED APPLICATIONS

This application is a 35 U.S.C. §111(a) continuation of PCT international application serial number PCT/US2009/051290 filed on Jul. 21, 2009, incorporated herein by reference in its entirety, which is a nonprovisional of U.S. provisional patent application Ser. No. 61/083,105 filed on Jul. 23, 2008, incorporated herein by reference in its entirety. This application is a continuation-in-part of U.S. patent application Ser. No. 12/840,065 filed on Jul. 20, 2010, incorporated herein by reference in its entirety, which is a 35 U.S.C. §111(a) continuation of PCT international application serial number PCT/US2009/032733 filed on Jan. 30, 2009, incorporated herein by reference in its entirety, which claims priority to U.S. provisional patent application Ser. No. 61/024,762 filed on Jan. 30, 2008, incorporated herein by reference in its entirety. This application is a continuation-in-part of U.S. patent application Ser. No. 12/363,079 filed on Jan. 30, 2009, incorporated herein by reference in its entirety, which is a 35 U.S.C. §111(a) continuation of PCT international application serial number PCT/US2007/075220 filed on Aug. 3, 2007, incorporated herein by reference in its entirety, which claims priority to U.S. provisional patent application Ser. No. 60/835,552, filed on Aug. 3, 2006, incorporated herein by reference in its entirety. Priority is claimed to each of the foregoing applications.

This application is related to PCT International Publication No. WO 2010/011676 published on Jan. 28, 2010, PCT International Publication No. WO 2009/097580 published on Aug. 6, 2009, and PCT International Publication No. WO 2008/017076 published on Feb. 7, 2008, each of which is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to diagnostic and interventional imaging using beams and detectors such as tomography, and more particularly to systems and methods for creating three dimensional cross sectional images of an object by the reconstruction of its projections that have been iteratively refined through modification in object space and Fourier space and permits object dose reduction and image enhancement.

2. Description of Related Art

Conventional tomography is an imaging technique that produces a cross-sectional 2D or 3D image of the internal structures of an object through planar projections. The typical tomography apparatus contains a radiation source and a detector that is rotated around an axis extending perpendicularly from the plane of the examination table. Projections of the patient or object are normally taken at equal angle intervals such that the angle of the radiating source with respect to the isocenter of the scanner changes by a fixed amount from one projection to the next. Images have been produced from several different beam sources including x-rays, electrons, gamma rays, ions, neutrons, sound waves and others.

One significant problem encountered with traditional tomographic imaging systems is the degradation of resolution and other image quality parameters due to the occurrence of missing or incomplete sets of projection data. Missing projection data can arise from radiation dose restrictions or from practical mechanical limitations in the imaging procedure or imaging system. One example is the missing wedge problem that occurs in electron microscopy, i.e., specimens cannot be tilted beyond ±70° and the data in the remaining ±20° projections are missing. These difficulties currently limit the resolution of the 3D imaging of cellular and organelle structures.

Since the radiation dose is proportional to the number of projections that are taken, and since tomographic imaging naturally requires a high number of projections for a suitable reconstruction, common tomographic devices can impart a significant radiation dose to patients as a result of the imaging procedure. With the increasing popularity of medical x-ray CT and fluoroscopic interventional imaging procedures, the long term effects of exposing patients to such ionizing radiation is of increasing concern, especially for pediatric patients.

In addition to the problems of radiation dose and missing projection data, conventional image reconstruction algorithms suffer from inaccuracies from interpolation limitations. Since conventional tomography reconstructs a 3D object from a set of equally angled 2D projections, the manner of acquisition inherently forces the projection data into a polar format. Because the set of acquired projections are in polar coordinates and the object is in Cartesian coordinates, interpolation must be used in the reconstruction process either in object space or in Fourier space. Such interpolations may account for a large source of error from the reconstruction algorithm alone and result in a significant degradation of image quality as measured by the resolution, contrast, and signal to noise ratio.

Currently, the most widely used slice reconstruction algorithm is the filtered back projection (FBP). The filtered back projection scheme is computationally fast, but does not offer any solutions for the problem of excessive radiation dose exposure and the problem of image degradation due to missing projection data. In addition, FBP suffers from inaccuracies due to inherent interpolation problems that occur in the back projection process. As a result of the problem of missing projection data and the problem of interpolation, images reconstructed with the FBP method often contain artifacts that degrade the resolution and overall image quality.

For example, conventional FBP reconstruction algorithms merely give one solution from the entire solution set. Such reconstructions are well known to contain grainy unphysical noise which degrades the image quality and limits the visibility of low contrast objects. Furthermore, since the noise in the projections and resulting image is correlated to the particle fluence at the detectors, in order to manage the noise in the reconstructed image, high particle fluences are required for conventional methods, resulting in high radiation dose to patients.

In addition to FBP, other reconstruction algorithms exists that are not in general use because they are computationally expensive under practical imaging conditions and also suffer from the problem of interpolation, which reveals itself when the forward projection process is modeled into the system matrix. These methods are also very sensitive to experimental noise and often diverge under realistic noisy experimental situations if the noise is not correctly modeled into the algorithm.

It can be seen that, reconstruction algorithms currently existing in the art, such as Filtered Back Projection, are not mathematically exact and consequently may produce images of lower resolution, contrast, and signal to noise ratio than what may be possible. These introduce inherent errors in the reconstructed image that result primarily from the reconstruction algorithm itself as opposed to experimental error.

Some reconstruction algorithms, such as the Estimated Maximum algorithms and maximum a posteriori algorithms have been specifically developed to arrive at a less noisy solution through a maximization or minimization of some objective parameter relating to the image noise. However, such algorithms have not been incorporated into the clinic and are limited in their application and accuracy because 1) the noise must be physically modeled before hand, which in most cases may be difficult or impossible; 2) If accurate physical models are not used, the algorithms diverge resulting in worse reconstructions than produced by conventional imagers; and 3) The current algorithms are not capable of including physical constraints, which may change from one patient to another.

Furthermore, due to the degradation of image quality, conventional methods of tomography require a high dose of radiation to be administered to a patient to produce suitable images. Consequently, conventional methods have a significantly higher probability of inducing secondary effects such as radiation damage or carcinogenesis to the patient.

Accordingly, there is a need for a system and method for tomographic imaging that limits the exposure of the subject to potentially harmful or destructive radiation that is at the same time accurate, reliable and computationally practical. There is also a great need for devices and methods with higher resolution and image quality. The present methods satisfy these needs, as well as others, and are generally an improvement over the art.

BRIEF SUMMARY OF THE INVENTION

The present invention provides a system and method for use with any tomographic imaging system that reconstructs an object from its projections. By way of example, and not of limitation, some embodiments of the present invention provide methods for reducing the radiation dose that is imparted to patients in tomographic imaging systems, as well as methods for image enhancement (i.e. enhancement of image quality parameters such as resolution, contrast, signal to noise ratio) and scan acquisition time reduction through use of substantially fewer projections in the image reconstruction process. A primary application of these methods is for radiation dose reduction in medical X-ray Computed Tomography (CT/CAT) scanners. However, the methods can be applied to any tomographic imaging system such as variants of transmission CT (Fluoroscopy, Electron Tomography/Microscopy, Megavoltage CT, MicroCT, Proton CT) and variants of emission tomography (Positron Emission Tomography (PET), Single Photon Emission Computed Tomography (SPECT)) as well as other modalities such as ultrasound.

The number of projections that can be acquired in the typical tomographic imaging system is limited by factors such as patient dose, time, and limitations in the scanner design which results in a portion of the projection data that is missing from a scan. The missing projection data can result in decreased resolution and produce artifacts that degrade the image quality of the reconstructed image. The present invention is an iterative reconstruction method capable of solving for a significant portion of the missing projection data. In one embodiment, the invention presents a method to eliminate interpolations present in conventional tomography. The method has been experimentally shown to provide higher resolution and improved image quality parameters over existing approaches. A primary application of the method is dose reduction since the present invention can produce an image of a desired quality with a fewer number projections than conventional methods.

Generally, embodiments of the invention make use of an iterative algorithm that solves for the missing projections and inaccessible data points during the reconstruction process. Once the experimental projection data from the imager is obtained, the projection data is reformulated so that it can be used in accordance of the Fourier Slice Theorem, and optionally, the oversampling method. By applying one of several possible types of Fourier transforms to each projection, a set of Fourier slices in Fourier space can be calculated and placed on an appropriate Fourier space grid in accordance to the Fourier Slice Theorem.

The missing projection data may be filled in by assigning random or preconditioned values to the missing Fourier space data, for example. The missing data is calculated and the image is reconstructed from the Fourier slices by using inverse and forward Fourier transforms to iterate back and forth between object space and Fourier space while modifying the data before each transform. The modifications in Fourier space may include making the resulting Fourier space data of the given iteration consistent with the transformed experimental projection data. The modifications in object space can consist of making the pixel (or voxel) values of the object data provided by the inverse Fourier space conform to a set of user defined values and/or conditions. The cycle of refinement will continue until a termination condition is satisfied and a final image is provided.

According to one embodiment of the invention, a method of tomography is provided with the steps of 1) obtaining projection data; 2) generating a Fourier transform of the projections at a plurality of angles and slice locations; 3) placing the transformed projections onto a grid in Fourier space; 4) performing an initializing modification of Fourier space; 5) performing an inverse transformation of said Fourier space data to provide an object space image; 6) refining said object space image; 7) modifying said object space image to produce a modified object space image; 8) performing a forward Fourier transformation on said modified object space image to produce Fourier space data; 9) refining the Fourier space data; 10) modifying said Fourier space data to produce a modified Fourier space data; and 11) applying said inverse Fourier transformation, modification, forward Fourier transformation and modification steps iteratively to the said modified Fourier space data until a termination condition is satisfied to provide a final image.

The refinement steps may be performed before or after the modification steps or in combination. The method may also include an initial refinement of the projections before the projection data enters the cycle in one embodiment. The refinements may include mathematical transformations such as denoising, deconvolution, deblurring, image restoration, and/or filtering transformations in the modifications and similar user defined mathematical transformation.

According to another aspect of the invention, a method is provided to dynamically determine the patient's/object's surroundings and then use the patient's/object's surroundings to aid the reconstruction process.

Another aspect of the invention is to provide a method of dose reduction.

Another aspect of the invention is to provide for image enhancement.

Another aspect of the invention is to provide for increased scan speeds by reducing the number of projections or flux needed for a given image quality.

In another aspect of the invention, a method that determines the expected values of the patient surroundings and utilizes these values to aid in the reconstruction process.

Since the number of projections is proportional to patient dose and/or scan time in such systems as transmission computed tomography, dose reduction and/or decreased scan time can be achieved through the use of the present invention. It will further be appreciated that all of the methods described herein can be used in any computerized tomographic imaging system including, but not limited to, all forms of transmission CT (x-ray CT, fluoroscopy, electron microscopy, etc.) and all forms of emission CT (SPECT, PET, etc.) In one embodiment, the boundaries of the patient are identified using anatomical information that is obtained from another imaging modality, such as MRI or x-ray CT scan.

According to another aspect of the invention, one method is provided comprising the steps of: (a) determining the regions in the field of view that do not correspond to the patient and/or radioactive sources for each slice of the reconstruction, and then (b) utilizing this information by such methods as pushing the voxel values in these regions to values corresponding to the proper value of the gas surrounding the patient or zero activity.

One embodiment of the invention provides a method for reconstructing an image of an object from its projections, obtaining projection data; generating a Fourier transform of the projections at a plurality of angles and slice locations; placing the transformed projections onto a grid in Fourier space; performing an initializing modification of Fourier space; performing an inverse transformation of said Fourier space data to provide an object space image; refining said object space image; modifying said refined object space image to produce a modified object space image; performing a forward Fourier transformation on said modified object space image to produce Fourier space data; refining said Fourier space data to product refined Fourier space data; modifying said refined Fourier space data to produce a modified Fourier space data; and applying said inverse Fourier transformation, refinement, modification, forward Fourier transformation, refinement and modification steps iteratively to the said modified Fourier space data until a termination condition is satisfied to provide a final image.

Another embodiment of the method for tomographic imaging, obtains equally sloped projection data from an imager; then denoises the projection data; pads the projection data with zeros with a suitable amount of zeros; generates a one dimensional Fractional Fast Fourier transform of the projections at a plurality of angles and slice locations; places the transformed projections onto a pseudopolar grid in Fourier space; stores the locations and values of the Fourier transformed projections; performs an inverse two dimensional Pseudopolar Fast Fourier Transform of each 2D slice in Fourier space to provide object space data; refines the object space data to produce refined object space data; modifies the refined object space data to produce a modified object space data; and performs a forward two dimensional Pseudopolar Fast Fourier Transform of each 2D slice of object space data to produce Fourier space data; modifying said Fourier space data to produce a modified Fourier space data; and applies the inverse Fourier transformation, modification, forward Fourier transformation and modification steps iteratively to the said modified Fourier space data until a termination condition is satisfied to provide a final image.

According to a further aspect of the invention, a method is provided that applies first and second refinements of the object space data during successive iterations between object space and Fourier space. For example, the first refinement could be a denoising transformation and said second refinement could be a deconvolution transformation. Likewise, different refinements may be used to refine the Fourier space in successive iterations.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the methods generally shown in FIG. 1 through FIG. 7F and the associated devices used to perform the methods. It will be appreciated that the apparatus may vary as to configuration and as to details of the parts, and that the method may vary as to the specific steps and sequence, without departing from the basic concepts as disclosed herein.

The present invention relates to improved computed tomographic imaging systems that mathematically reconstruct cross-sections of an object from its projections. The number of projections and the exposure of a subject to ionizing radiation such as X-rays can be substantially reduced by reducing scan times through imaging with fewer projections and reduced image noise without losing the fine image features in the process.

Generally, the method is a direct Fourier based iterative scheme that is termed equally sloped tomography. The preferred scheme iterates back and forth between object and Fourier domains with a variety of refinements and constraints enforced in both domains to produce an image. The preferred method uses a new form of the fast Fourier transform (FFT) called the pseudo-polar Fourier transform (PPFT), in which the grid points in the Fourier domain are lying on the equally-sloped lines instead of equally-angled lines. It has been mathematically shown that the pseudo-polar Fourier transform is algebraically exact, geometrically faithful and invertible.

One embodiment of the method uses 'oversampling.' When a Fourier slice is sampled at a frequency finer than the Nyquist interval, the corresponding projection in object domain is surrounded by mathematical zeros. If the Fourier slices that are calculated from the measured projections are oversampled, the 3D object to be reconstructed should be surrounded with zeros. These mathematical zeros do not provide extra information about the 3D object but will help to extract the correlated information among the Fourier slices.

In the Fourier domain, the measured Fourier slices are updated in each iteration. In the object domain, a support is defined in order to separate the object from its surrounding zeros, and the voxels outside the support and the negative voxels inside the support are set to zeros. The algorithm converges to a solution which closely satisfies the experiential measurements and the physical constraints.

Between iterations, the data may also be refined with sub-transformations, such as denoising, deconvolution algorithms, filtering algorithms, smoothing algorithms, deforming algorithms, deblurring algorithms, and image enhancement algorithms, as determined by the user of the algorithm to further improve image quality and reduce the radiation dose of the subject. In another embodiment, computational time may be reduced and image quality increased with the use of alternative algorithms to the reverse pseudo-polar fast Fourier transform.

Figure 1:
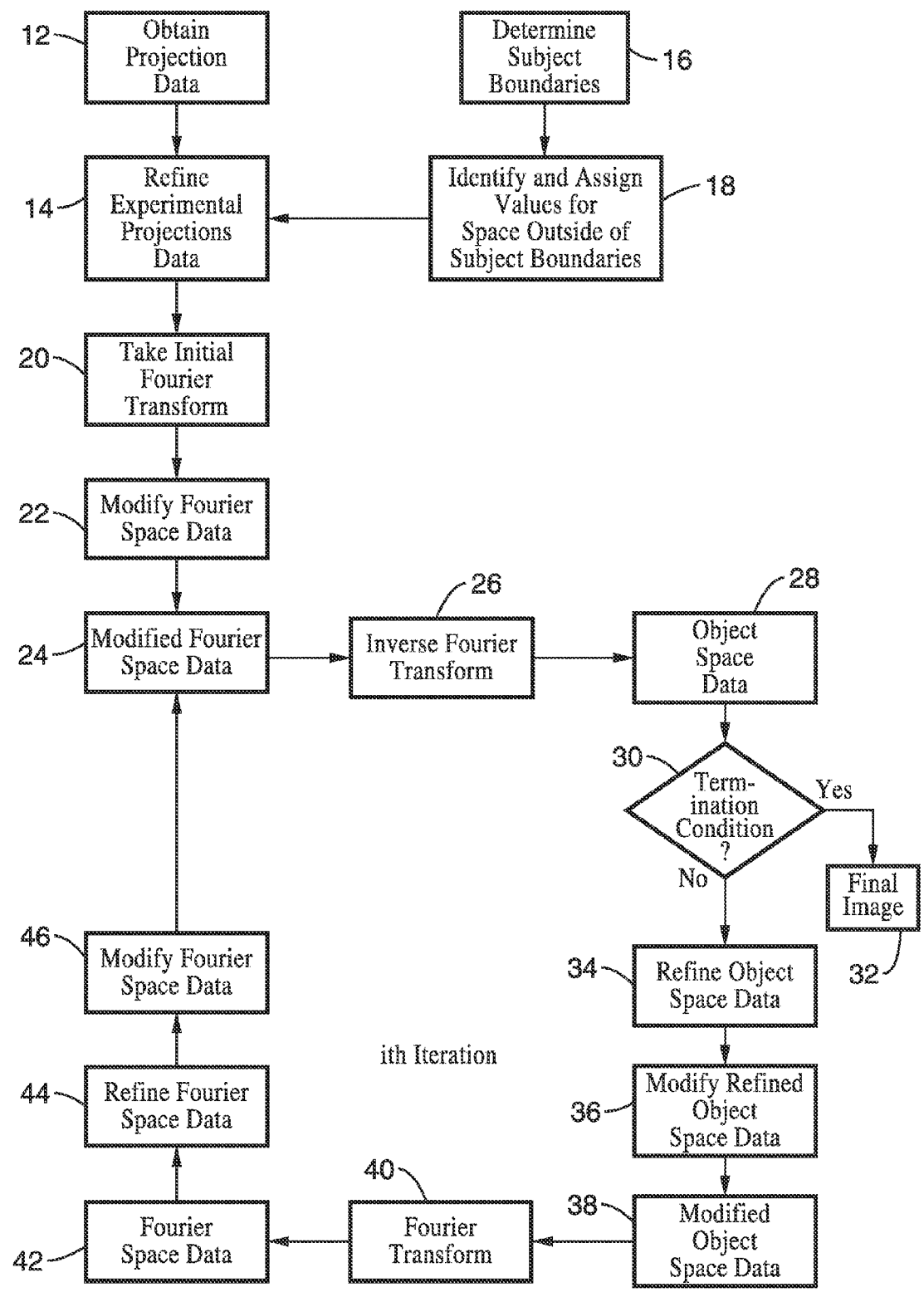
FIG. 1 is a flow diagram of a method for dose reduction and image enhancement using according to one embodiment of the invention.

Turning now to the flow diagram show in FIG. 1, one embodiment 10 of the invention is schematically shown. In FIG. 1, projection data from a parallel beam system is acquired at block 12 and may be recorded and processed with a computer or other recording device. For non-parallel beam systems, projection data may be acquired and then reformulated by a parallel-beam equivalent projection data set. Such reformulation at block 12 can be performed by mathematical transformations in an exact or approximate manner from the system geometry to produce an equivalent parallel beam geometry. The reformulation can also be performed by existing 'rebinning' algorithms present in the art which specifically change the projection data from the given system to a parallel beam equivalent system in an exact or approximated method. Another related method includes an interpolation of the sinogram along the desired parallel projection angular location to arrive at a parallel beam projection at block 12.

The acquired projection data may be recorded and stored or processed transiently in a computer apparatus configured for these purposes. Optionally, the initially acquired parallel beam data at block 12 can be refined through the application of a noise reducing mathematical transformation such a denoising, deconvolution, deblurring, image restoration, and or filtering transformation at block 14. Common examples of the mathematical transformations that can be used to refine the initial projection data at block 14 may include: 1) Wiener filtering/deconvolution and its many different variants; 2) Rudin-Osher-Fatemi (ROF) total variation (TV) algorithms and their variants; 3) Nonlocal means algorithms; 4) Penalized likelihood method; 5) Kalman filtering/deconvolution and its variants; 6) Speckle filtering; 7) Simple filters such as Gaussian filters, Laplacian filters, low pass filters, high pass filters, edge enhancing filters; 8) Anisotropic filters; 9) Deconvolution algorithms based on a known or user defined point spread function; 10) Wavelet denoising; 11) Neighborhood filters and the SUSAN filter; 12) Discrete universal denoiser; and 13) unsupervised information-theoretic, adaptive filtering as well as a variety of other transformations.

Optionally, the expected values of the surroundings of the patient or object may be determined and utilized in the image reconstruction process to further reduce computational time, radiation dose and the number of projections as well as increase the definition and enhance the final image. The typical scanner will attempt to resolve the whole field of view of the scanner including the background surroundings of the subject such as the surrounding air volume, the bed and the object support modules. This process creates the need for a higher number of projections for an adequate reconstruction of the subject and utilizes significant computational resources.

The characteristics of the scanner and the surroundings are identified and categorized and located in three dimensional space in the embodiment shown for some or all possible scan protocols and scanner configurations. This profile information may be stored in data storage for access and use with the other computer tomography programming. Accordingly, at block 16 and block 18 of FIG. 1, a profile of the scanner and subject surroundings is created in this embodiment. The produced profile will preferably account for the type of scanner that is used, the scan parameters and the characteristics of the subject that is being scanned. For example, conventional scanners may have one of several different types of beam sources including photons, electrons, protons, ions, neutrons and sound waves.

In one preferred embodiment, the expected voxel values of the subject's surroundings at Block 16 are determined by performing a set of scans without the subject in the scanner using many different scan parameters and scanner configurations in order to produce a reference data set with the approximate voxel values for each type of scan and scanner configuration. During the reconstruction process, the locations and nature of the patient's surroundings are determined by an initial reconstruction, a set of voxels may be designated as constraints, the expected values of these designated voxels are determined from the reference scans, and these expected values are then utilized to aid in the reconstruction of the subject scan.

Once the parallel beam data or parallel beam equivalent data has been acquired at block 12, optional boundaries and surroundings assigned at block 18 and optional initial pre-processing refinement at block 14 have taken place, a Fourier Transform of each projection is undertaken at block 20. The type of Fourier transform that is selected will depend on the type of grid in Fourier space that is desired. 'Fourier space' is defined as a space in which at least one Fourier transformation has been applied to a given data set. The Fourier space can also be constructed from other transformations in addition to the Fourier transform. In some situations, the Fourier space used here is similar or equivalent to the phrase 'frequency domain' or 'k-space' in the art. In one embodiment, the Fourier transform of the projections at a plurality of angles and slices at block 14 is a Fractional Fourier Transform set to match points and lines of a pseudopolar grid for each angle in accordance to the Fourier Slice Theorem. Other computerized implementations of the FT such as the non-uniform Fast Fourier Transform (NUFFT) and the conventional Fast Fourier Transform (FFT), can be utilized at this point in accordance with the Fourier Slice Theorem.

Optionally, the Fourier space data of the projections may then be modified at block 22 of FIG. 1. Other supplemental transforms can also be applied to the projection data at this point as part of the initial Fourier space modifications. For example one supplemental transform includes a Fourier Transform across all slices in the Fourier space to correlate the Fourier space data. Modifications at block 22 may also include filling in missing projection data by assigning values to non-experimental locations in Fourier space. The non-experimental locations can be visualized as regions in Fourier space that the transformed experimental projections do not cover when they are placed on the Fourier space grid. However, the non-experimental regions can be more generally defined as locations which the user or the algorithm designates as non-experimental.

The Fourier transforms of the refined projections are placed on a grid in Fourier space at block 24. For example, a pseudopolar grid has points that sit at the intersections of linearly expanding concentric squares with angularly spaced rays. In contrast to conventional methods of tomography, one embodiment of the present invention acquires the data in such a manner that the projections lay (when converted into parallel geometry) partially or fully along a selected number of equally sloped lines of a pseudopolar grid. The projections at each angle are then exactly mapped to their corresponding lines on the pseudopolar grid in the Fourier space, preferably using the Fractional Fast Fourier Transform (FrFFT). Through this embodiment, interpolations that are present in conventional methods of tomography can be eliminated.

The placement of transformed projections onto a grid in Fourier space may also be performed with an exact or approximate mathematical transformation, or by interpolating the location and values of a transformed projection on the Fourier space grid. The placement of transformed projections onto a grid in Fourier space may also be performed by the Gridding method. The present invention is not restricted to any specific grid in Fourier space. Other grids that may be used for the Fourier space data include Cartesian type, polar type, 3D polar (i.e., spherical) type, 3D pseudopolar and others.

The modified Fourier space data begins an iterative process at block 24 that is able to solve for the missing/incomplete projection data and or experimentally inaccessible data points in Fourier space. These missing projection data typically arise in computed tomography due to the limitations in administered dose or system design or limited resources in conventional applications. Shifting between Fourier space and object space while refining and modifying the data in each space between shifts permits iterative refinements to the data until a final image is reconstructed. The resolution is improved as a result of removing the degradation of image quality that is present in the art due to missing projection data.

At block 26 of FIG. 1, an inverse Fourier transform is preferably performed upon the Fourier space data of block 24 to provide data in real or object space at block 28. Different types of inverse Fourier transforms may be used at block 20 depending on the Fourier and object space grids that are used. For example, if the Fourier space is on a pseudopolar grid and the object space is on a Cartesian grid, the inverse pseudopolar fast Fourier transform (IPPFFT) may be used. Alternatively, if both grids are Cartesian, a conventional inverse FFT routine may be used. The inverse FT can be performed slice by slice or together at once or on grouped subsets of slices. The slice by slice method may be preferred as it easily allows for parallel computing by distributing subsets of slices across different computers.

Accordingly, the missing projection data is calculated and the image is reconstructed from the Fourier slices by using inverse and forward Fourier transforms to iterate back and forth between object space and Fourier space while refining and modifying the data before each transform. In another embodiment, alternative iterative algorithms are used as a substitute for the Inverse Fourier transformation at block 26 in the scheme shown in FIG. 1.

In the iterative cycle illustrated in FIG. 1, the object space data obtained at block 28 can be refined at block 34 and then modified at block 28 to provide refined and modified object space data at block 38. The refinements at Block 34 can be mathematical transformations such as denoising, deconvolution, deblurring, image restoration, and filtering transformations in the modifications at block 36.

Object space data modifications in general make the object space pixel values conform to defined constraints and thereby provide an efficient method to iteratively solve the reconstruction problem in a manner consistent with the selected constraints. An object space pixel can be made to conform to an expected or desired value (i.e., a constraint) in any mathematical manner. One of the simplest and most common methods for achieving this is by replacing the pixel value by a value that is dictated by the applied constraint. For example, if a constraint dictates that a specific pixel should have the numerical value of zero, the value of the pixel may be changed to zero in the given iteration.

The modified object space data at block 38 is then subject to a Fourier transform at block 40 to produce Fourier space data at block 42. The Fourier space data obtained at block 42 can be refined at block 44 and modified at block 46 to produce modified Fourier space data at block 24. The iterative cycle can begin again with the application of an inverse Fourier transform of the Fourier data to produce slightly refined object space data at block 28. The cycle can proceed until a termination condition is satisfied at block 30 such as a predetermined number of iterations or a monitored error reaches a certain value. A final image 32 can be produced from the results of the refined data.

The termination of the cyclic process is evaluated at block 30 to determine if a termination event has occurred. One termination event can be the occurrence of a predetermined number of iterations. Another termination event can be the occurrence of a monitored error or image quality parameter function. Yet another termination event can be the occurrence of situation where the error or image quality parameter has not improved in a prescribed number of iterations. In this type of method, the final image may be produced by inverting the Fourier space data corresponding to the best error or image quality parameter, and optionally cropping the object space in accordance to the oversampling used.

Furthermore, the final image 32 does not necessarily have to be based upon the calculated data from the last iteration. In general the final image can be based on the data from previous iterations, or new data that is formed by combining data from previous iterations. For example, the final image can be the average of the object space data from a number of different iterations. In addition, the termination event can be made to occur at any step in the iterative cycle. The final image 32 can be based upon any step of the iterative process.

Generally, the refining steps at block 14, block 34 for object space and block 44 for Fourier space can be represented mathematically by the transformation $_{\#}M^i$, where # designates the step in the cycle, i designates the iteration number. For example, as the first refining step (step 1) at block 14 is an initializing step and outside the loop, $_1M^i$ only exists for i=0.

The use of these indices reflects the important fact that the transformation generally differs and depends on the step type and iteration number.

Figure 2:
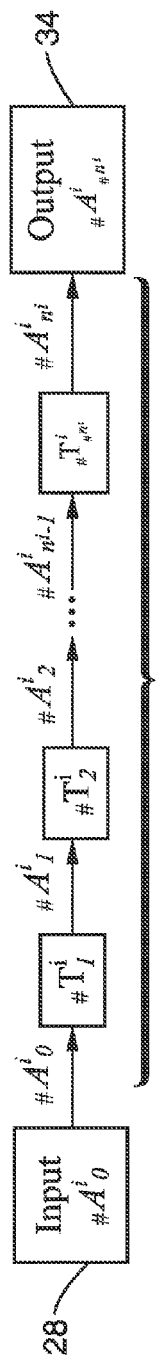
FIG. 2 depicts one type of sub-transformation algorithm according to the invention.
Figure 3:
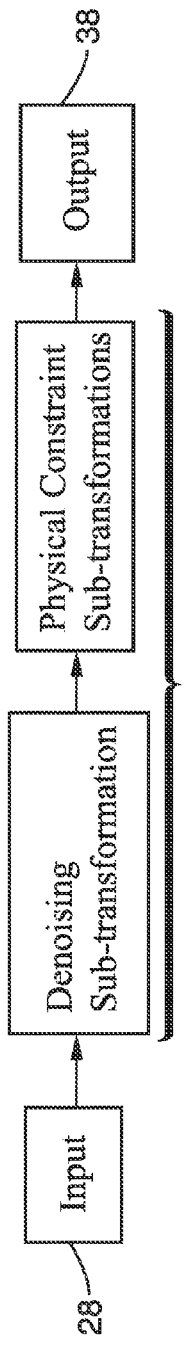
FIG. 3 is a flow diagram of one embodiment of the method for dose reduction and image enhancement with the application of a denoising sub-transformation applied before modification sub-transformation as shown in FIG. 1.
Figure 4:
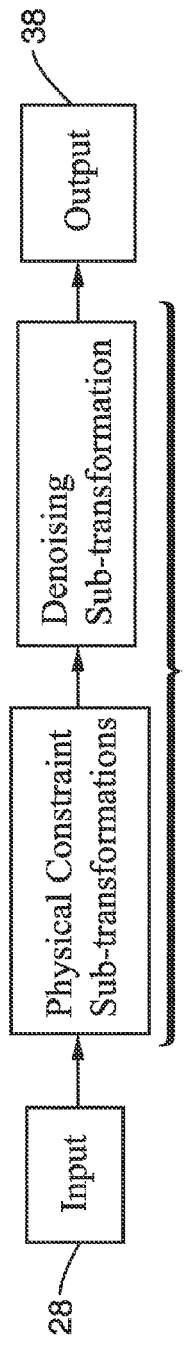
FIG. 4 is a flow diagram of one embodiment of the method for dose reduction and image enhancement with the application of a denoising sub-transformation applied after modification sub-transformation according to an alternative embodiment of the invention.

Referring also to FIG. 2 through FIG. 4, the refinement steps shown in block 14, block 34 and block 44 and the modification steps of block 22, 36 and 46 can be applied to the iteration sequentially, simultaneously or in reverse order to produce an output. Given an input array A, the transformation $_\#M^i$ acts on A to produce a modified array given by A', where $A'=_\#M^i(A)$. It should be noted that the input and output arrays for the step at block 14 (step 1) and block 44 (step 3) correspond to Fourier data, and therefore they are typically complex, while in the step at block 34 (step 2) has arrays that correspond to object space data which is typically real. The overall modification $_\#M^i$ can be considered to be composed of a number of other sub-transformations $_\#T^i_j$ resulting in the overall modification such that $_\#M^i(_\#A^i_0) =_\# T^i_{\#n^i}(_\#T^i_{\#(n-1)^i}(\ldots(_\#T^i_1(_\#A^i_0))\ldots) =_\#A^i_{\#n^i}$, the overall modifying transformation can be considered as $_\#n^i$, separate sub-transformations (the # and i reflecting the fact that number of sub-transformations is different for each iteration and each corresponding step #). This process is schematically portrayed in the block diagram shown in FIG. 2 and indicated as sub-transformations in FIG. 3 and FIG. 4. The refining steps in the cycle can be conducted in conjunction with or sequentially with the application of physical constraints in the cycle shown in FIG. 1. As an example, in step 2, a first sub-transformation, $_2T^i_1$, can be the application of denoising algorithm such as the Rudin-Osher-Fatemi (ROF) total variation (TV) algorithms to reduce the image noise of the input.

Examples of the sub-transformations in FIG. 2 through FIG. 4 can also include the physical constraints described previously. The positivity constraint, for example, can be regarded as another sub-transformation, say $_2T^i_2$, which given an input array, outputs a modified array with the negative values set to 0, or closer to 0.

Another sub-transformation in the data modification can be the application of constraints regarding the subject patients' surroundings in accordance with block 16 and block 18 so that a sub-transformation, such as $_2T^i_3$, replaces some elements of the input array corresponding the surroundings to the desired value of the surrounding information. Then according the to the embodiment of FIG. 1, the 'modifying of the object space data' in block 36, can be performed by the equation: $_6M^i(_6A^i_0) =_6T^i_3(_6T^i_2(_6T^i_1\ (_6A^i_0))) =_6A^i_3$ in each iteration i, which results in driving the algorithms to a less noisy state consistent with the ROF de-noising algorithm, positivity constraint, surrounding constraints, and the experimental data.

In another embodiment, the user can determine the number of sub-transformations and the location in the cycle that the sub-transformations are applied as well as the type of sub-transformations that are applied to the iteration. For example, a denoising sub-transformation may be applied only in a limited number of iterations or steps to give more importance to the other sub-transformations in the cycle. Alternatively, multiple or different types of mathematical sub-transformations can be performed for each iteration, and the modification in each iteration can differ from other iterations. The pre-cycle refinement at block 14 can be of a different type than the sub-transformations at block 44, for example.

As further example, the (step 3) refinement at block 44, could have a first sub-transformation that makes the Fourier data consistent with experimentally measured Fourier transformed projections by replacing the positions corresponding to experimental data by the measured Fourier transformed projections that is followed by a second transformation, which denoises the Fourier space data through an adaptive Wiener filter or multiplication by other filtering function that suppresses the high frequency data in the second iteration. Analogous to the previous modification, the overall modification may be given by: $_8M^i(_8A^i_0) =_8T^i_2(_8T^i_0)) =_8A^i_3$.

The general structure of the embodiment shown in FIG. 2 through FIG. 4 is to include a denoising sub-transformation, in conjunction with other sub-transformations such as positivity and surrounding constraints, which are identified collectively as physical constraint sub-transformations in FIG. 3 and FIG. 4, to produce a modified object space image at block 38. In the embodiments shown, the user can designate which iterations the denoising sub-transformation is to be applied in conjunction with the type of physical constraint sub-transformations that are applied or in what order. The user can also determine which iterations the physical constraint sub-transformations are to be applied without the denoising sub-transformation. For example, the denoising sub-transformation can be included in all the iterations, or included in every n iterations, or included for several iterations in cycles, or included in only in the first m iterations, or included only when the error function is above some value, or only up to max-k th iteration where max is the maximum number of iteration and k is a certain user defined iterations. The order by which the denoising and physical constraint sub-transformations are applied during each iteration can be designated by the user. Two possibilities are shown in the block diagrams illustrated as FIG. 3 and FIG. 4.

It can be seen that there is substantial variation in the user selected refinements and physical constraints that can be used. In one embodiment, the 'denoising sub-transformation' is an adaptation of the Rudin-Osher-Fatemi (ROF) total variation (TV) algorithm or an adaptation of the Non-Local Means algorithm. In another embodiment, the 'denoising sub-transformation' is and adaptation of a Wiener filtering/deconvolution such as the adaptive Wiener filter or an implementation of sinogram denoising methods.

In these illustrative embodiments, the strength of the denoising sub-transformation can be designated by the user as a function of iteration number. For example, with the adaptive Wiener filter the user can designate a window size which increases the denoising behavior as the window size is increased. Typically the smallest window size producing a denoising is used in order to avoid blurring or loss of resolution. For the ROF and Non-Local means embodiments, the strength of the denoising is typically designated by an input parameter λ. An efficient guide for choosing lambda is to use a lambda that gives the highest correlation to the same image denoised by adaptive Wiener filter with a given window (which can commonly be the smallest window size).

However, in some situations the denoising sub-transformation (including, deconvolution, filtering, smoothing, deforming, deblurring, image-enhancement algorithms) may either over-simplify the input array or introduce unphysical artifacts. In these situations, a preferred embodiment includes modifying the output of such a sub-transformation so that the output is averaged or combined with the input array of these sub-transformation and or corresponding arrays from previous iterations. In general mathematical terms, if one such sub-transformation (for example a denoising sub-transformation) is denoted $T_D$ with its input and output are denote as $A_{In}$ and $A_D$, respectively, and the output array from the same cycle step of one of the previous iterations is $A_{Prev}$, then instead of $T_D$ a modified sub-transformation, denoted as $T_{Mod}$, is used in place of $T_D$. $T_{Mod}$ mathematically combines the would be output of $T_D$ with $A_{In}$ and $A_{Prev}$ to produce a modified output array denoted $A_{Mod}$, two examples of such combinations include 1) weighted additive combination such that $T_{Mod}(A_{In})=(p\,A_D+q\,A_{In}+r\,A_{Prev})/(p+q+r)$, where the weights p, q, and r arbitrary scalars 2) weighted multiplicative combination such that $T_{Mod}(A_{In})=(abs((A_D)^p(A_{In})^q(A_{Prev})^r))^{(1/(p+q+r))}$, where the weights p, q, and r arbitrary scalars, and abs is the absolute value function to be used if the sum p+q+r is even. As a result of the use of such a modified sub-transformation, the over-simplification or unphysical artifacts of $T_D$ can be significantly reduced. Although in general the user can define $T_{Mod}$ in a variety of ways (for example by choosing different values for the weights p, q, and r), we have confirmed through simulations and experiments that a simple combination such as $T_{Mod}(A_{In})=(A_D+A_{In})/2$, or $T_{Mod}(A_{In})=(A_D A_{In})^{(1/2)}$, is suitable for most situations.

Embodiments of the present invention are described with reference to flowchart illustrations of methods and systems according to embodiments of the invention. These methods and systems can also be implemented as computer program products. In this regard, each block or step of a flowchart, and combinations of blocks (and/or steps) in a flowchart, can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts support combinations of means for performing the specified functions, combinations of steps for performing the specified functions, and computer program instructions, such as embodied in computer-readable program code logic means, for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s).

The invention may be better understood with reference to the accompanying examples, which are intended for purposes of illustration only and should not be construed as in any sense limiting the scope of the present invention as defined in the claims appended hereto.

EXAMPLE 1

In order to demonstrate the functionality of the invention and the general principles behind the refining sub-transformations, comparative reconstructions of a phantom were conducted. In the embodiments tested, the object space was placed on a Cartesian grid, and the Fourier space was on a pseudopolar grid that was oversampled by a factor of 2 with respect to the object space grid. A Fourier transform of the acquired projections at a plurality of angles and slice locations was performed by a fractional fast Fourier transform with parameters such that when the transformed projections were placed onto a grid in Fourier space the Fourier slices were placed on the closest pseudopolar grid precisely. However, in this example the initializing modification of Fourier space was not performed.

The inverse transformation of said Fourier space data to provide object space data was performed by an Inverse Pseudopolar Fast Fourier Transform (PPFFT$^{-1}$) and forward Fourier transformation was performed by a Pseudopolar Fast Fourier Transform (PPFFT).

To demonstrate the effect of the refinement step, the Fourier space data modification consists of just one sub-transformation replacing the values at locations of the experimental Fourier slices with experimentally measured Fourier slices. The algorithm was terminated once either a certain user designated number of iterations are reached, or the error function does not decrease by certain user designated percentage.

Figure 5B:
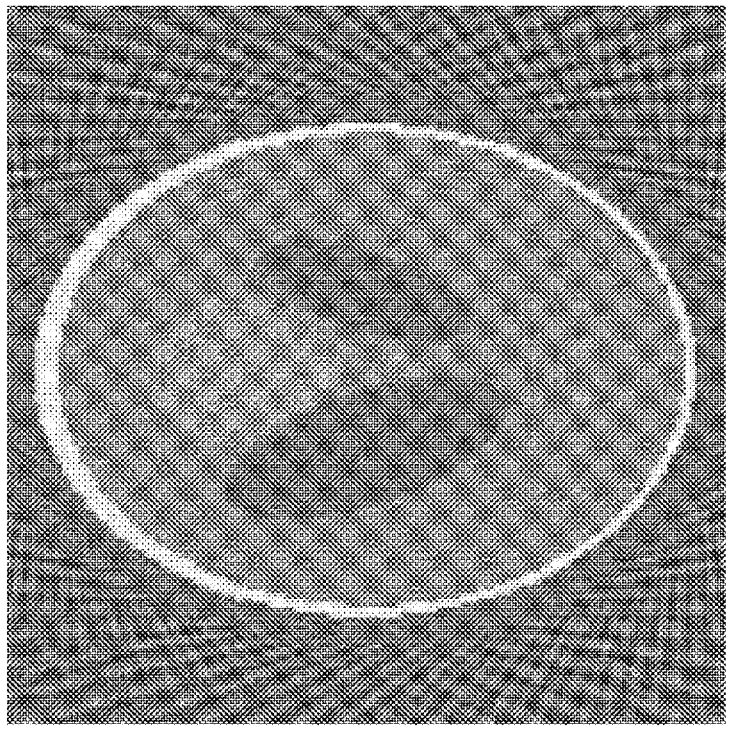
FIG. 5A-5D depicts the tomographic reconstruction of a 160×160 Shepp-Logan phantom using 45 projections from different imaging modalities for comparison.
Figure 5A:
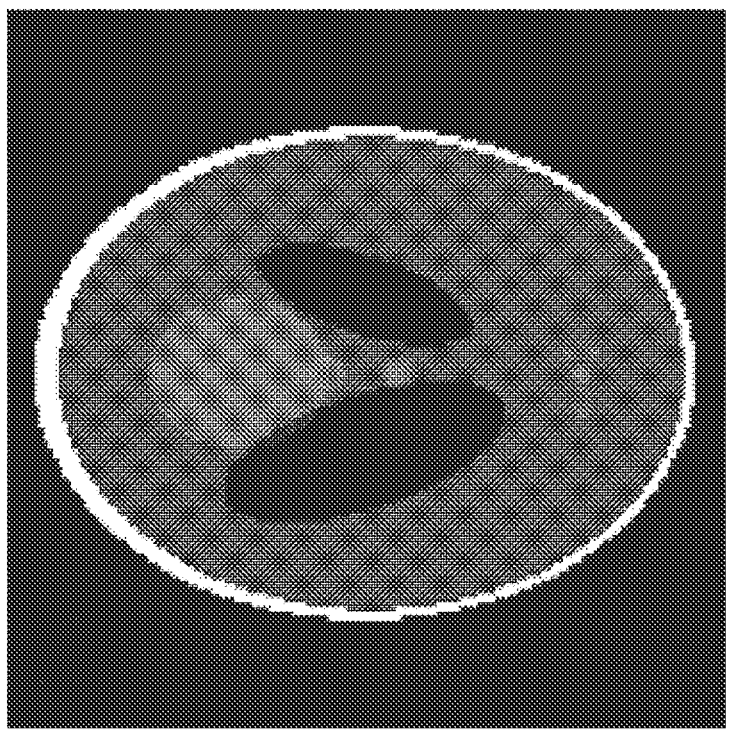
Figure 5D:
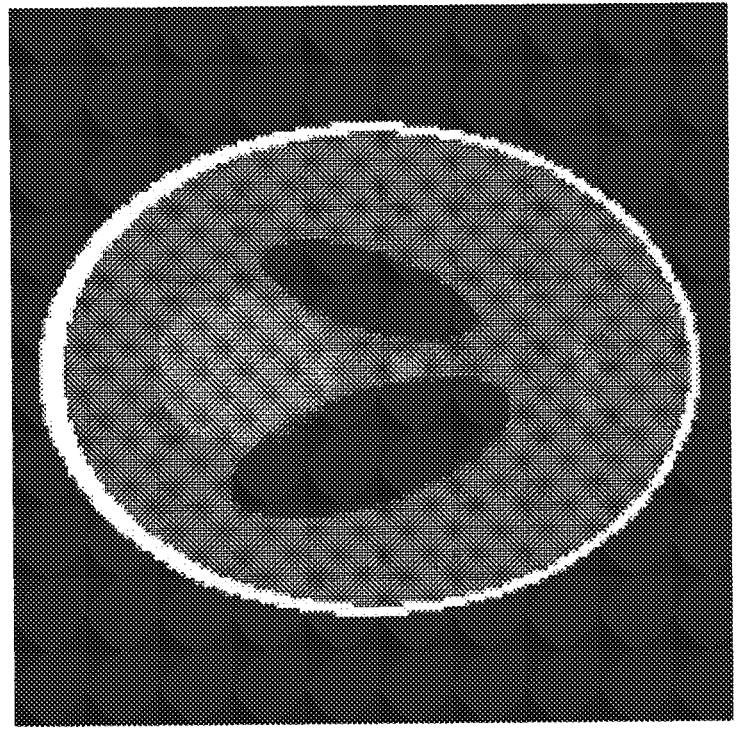
Figure 5C:
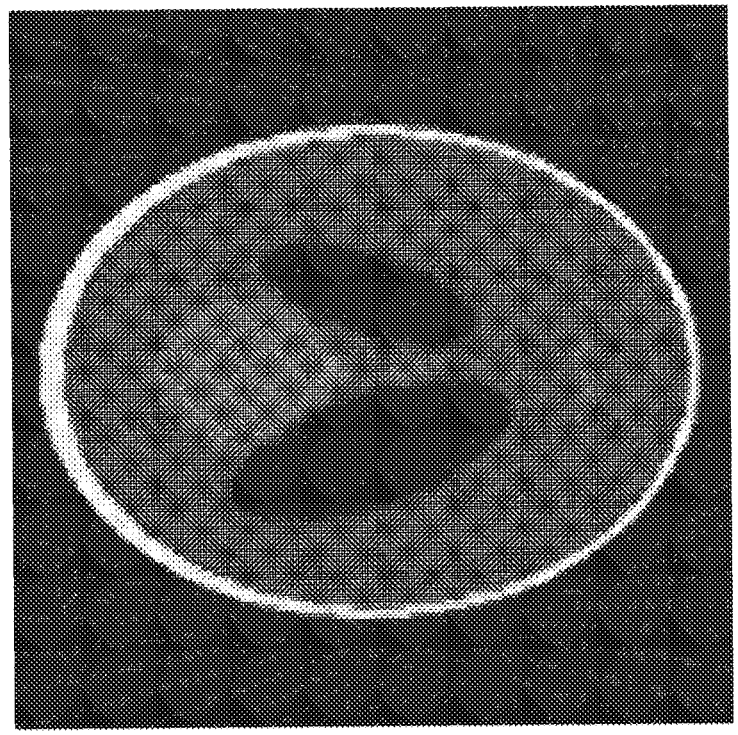

Referring now to FIG. 5A through FIG. 5D, the results of the configuration using a denoising sub-transformation included in each iteration as described above and shown schematically in FIG. 3 are provided. In FIG. 5A-5D, different methods are tested on tomographic reconstruction of a 160×160 Shepp-Logan phantom using 45 projections. FIG. 5A displays the phantom. FIG. 5B displays the conventional reconstruction using a standard filtered back projection known in the art for comparison. The results of the equally-sloped tomography method without the refinement step are shown in FIG. 5C. FIG. 5D displays the results where the ROF algorithm is utilized in each iteration, and the iterations are stopped once the error does no decrease further by more than 1%.

It can be seen that the results shown in FIG. 5C are significantly improved over the result from the conventional filtered back algorithm, but it still maintains some noisy artifacts not present in the test phantom. However, with the refinement step a nearly perfect reconstruction is achieved and the artifacts seen in FIG. 5C have been removed using the methods of the invention.

EXAMPLE 2

Figure 6B:
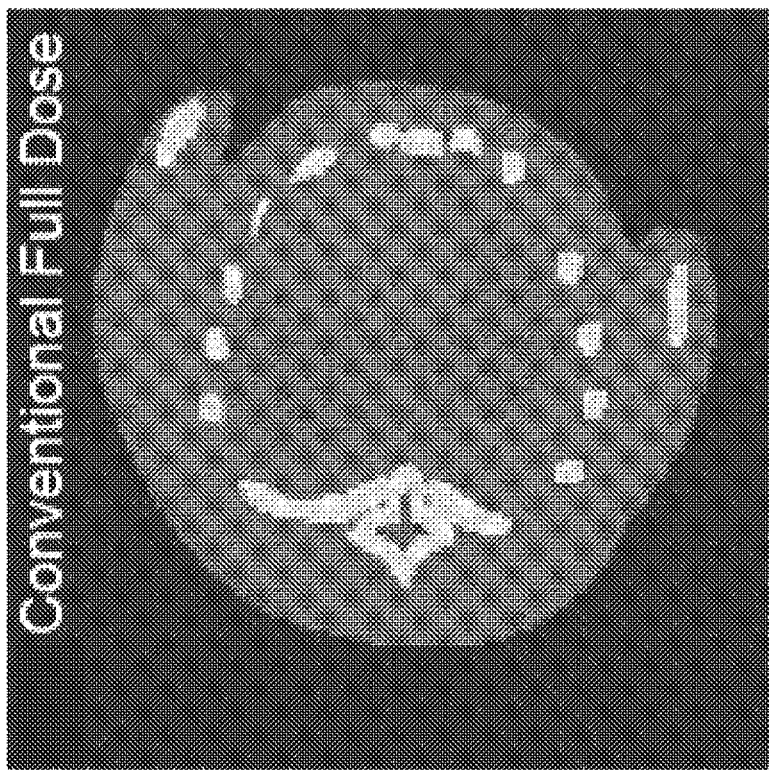
FIG. 6A-6D depicts the tomographic reconstruction of a mouse phantom using 180 projections from different imaging modalities for comparison.
Figure 6A:
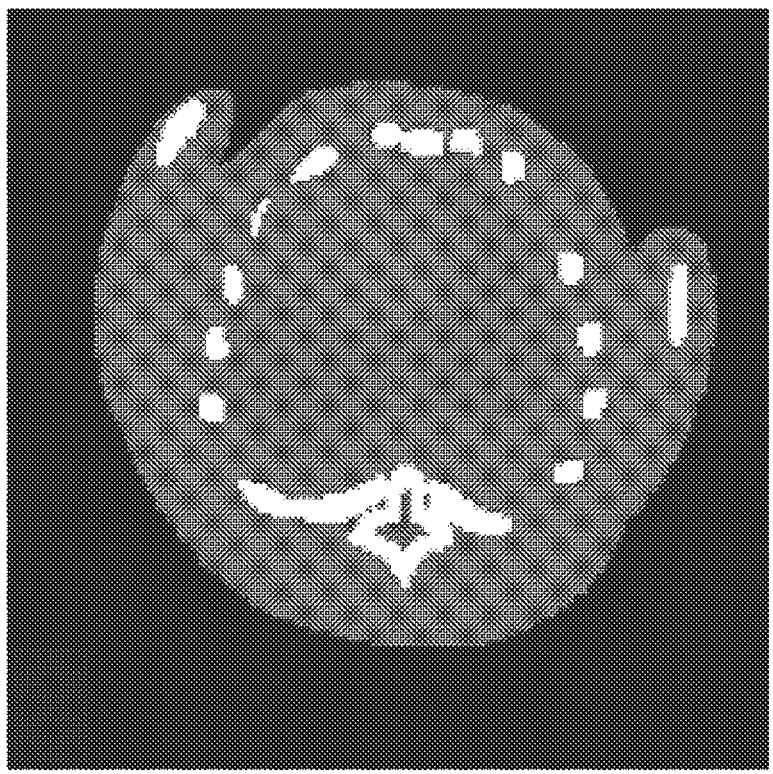
Figure 6D:
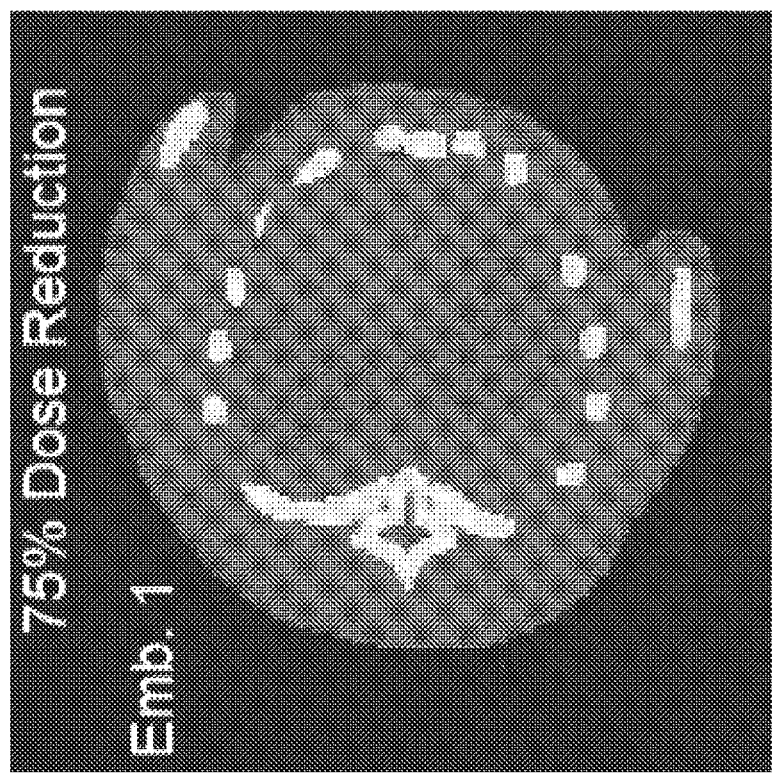
Figure 6C:
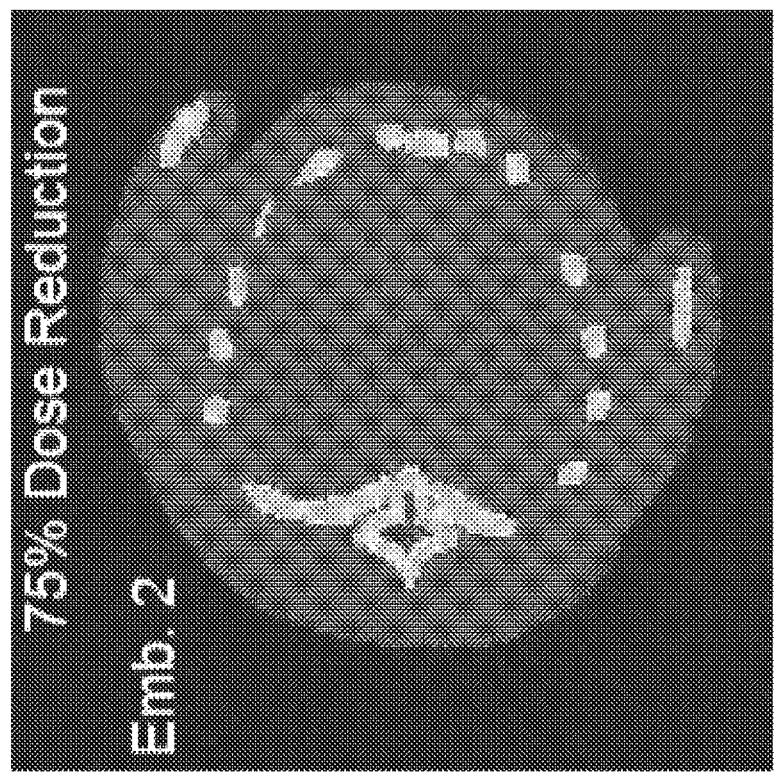

In FIG. 6A through FIG. 6D, the noise is simulated in the projections and the tomographic reconstructions are performed on a mouse phantom. FIG. 6B shows the conventional reconstruction at full dose defined by 180 projections and 12000 photon flux. For comparison, FIG. 6C demonstrates the embodiment shown in FIG. 4 using the adaptive Wiener filtering (applied in each iteration) with 90 projections and 6000 photons, i.e. 75% less dose. FIG. 6D demonstrates the results from the configuration shown in FIG. 3 as previously discussed with 90 projections and 6000 photons, i.e. 75% less dose than required in the art.

To quantify the image quality, the signal to noise ratio (SNR) was calculated for different tissues. For the conventional at full dose (FIG. 6B), the SNR is calculated to be: Bone: 13.2646 Heart: 9.349 Soft Tissue: 8.7087 Lung & Skin: 8.3156 VF: 4.8091 Air: −0.22644; for preferred embodiment 2 (FIG. 6C), the SNR is calculated to be: Bone: 17.7948 Heart: 17.7376 Soft Tissue: 12.4765 Lung & Skin: 11.6961 VF: 5.4195 Air: 0.76365.

For the embodiment shown in FIG. 3 and the results in FIG. 6D, the SNR was calculated to be: 23.1601; Heart: 22.1794 Soft Tissue: 16.1466 Lung & Skin: 15.2858 VF: 6.8594 Air: 0.80871. These results show that the preferred embodiments in this invention, with even 75% lower dose, result in an image quality significantly better than the conventional FBP reconstruction as is quantified by the fact that all tissues for the embodiments have significantly higher SNR than the conventional (even at 75% less dose).

EXAMPLE 3

Figure 7A:
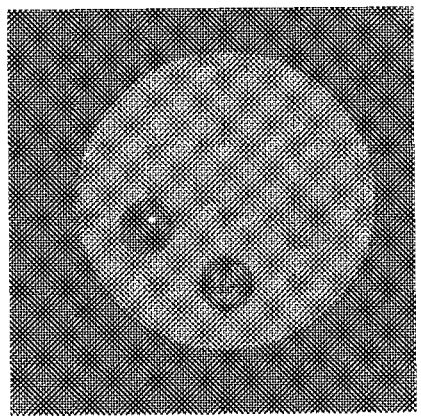
FIG. 7A and FIG. 7F depict comparative tomographic reconstructions of an image quality phantom using synchrotron x-ray irradiation.
Figure 7B:
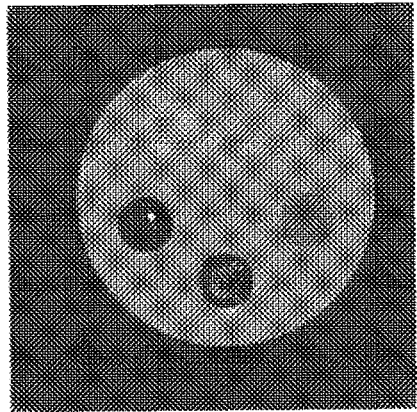
Figure 7C:
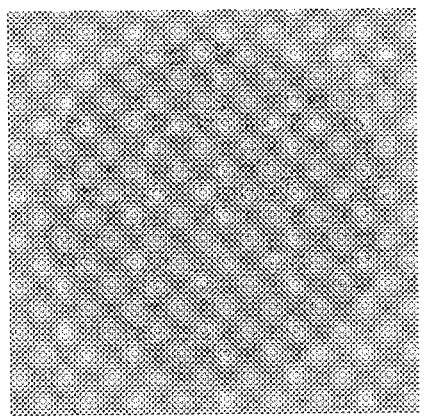
Figure 7D:
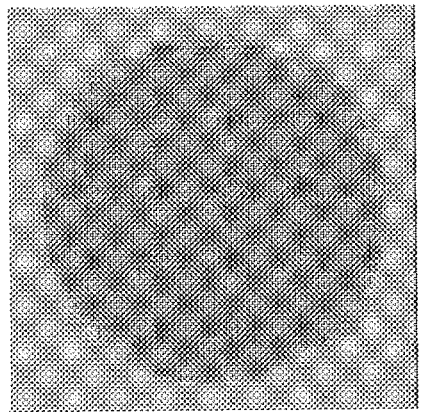
Figure 7E:
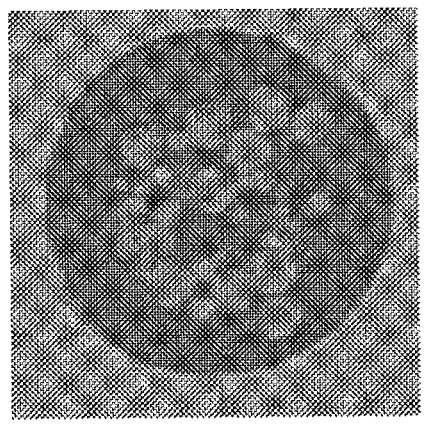
Figure 7F:
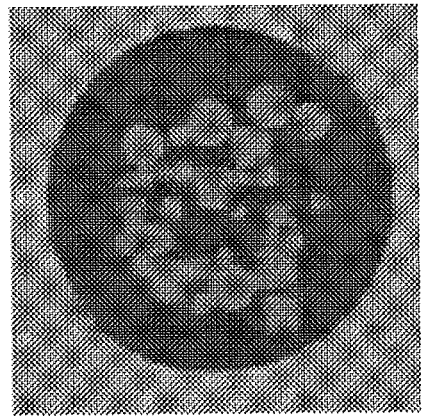

One of the primary purposes of the invention of dose reduction in medical imaging that can be achieved by reducing either the photon fluence and or number of projections and using the methods is shown in FIG. 7A through FIG. 7F. The methods of this invention are experimentally demonstrated in FIG. 7 with comparative reconstructions of an image quality phantom using synchrotron x-ray irradiation. Tomographic projections were acquired at 200 equal angle intervals. The images to the left represent the conventional reconstruction and the images to right represent reconstruction via preferred embodiment 1, with experimental projections mapped onto nearest pseudopolar line as described above. The results demonstrate that the methods described here have driven the reconstruction to a less noisy state consistent with the actual phantom and experimental projections. FIGS. 7C and 7D demonstrate that the contrast is significantly improved with the use of the methods. The improvement is quantified by reference to the contrast to noise ratio which is 1.8 for the conventional reconstruction and 7.7 for embodiment shown in FIG. 3 and in FIG. 7D. It can be seen that results that the refining step did not result in a lower resolution and FIGS. 7.E and FIG. 7F are of comparable resolution, with FIG. 7F void of artifacts.

These examples demonstrate that through the present invention, an object can be reconstructed with a reduced number of projections (hence in general, a reduced patient dose, and scan time) than with conventional methods. As a result, the same number of projections as conventional methods can be used to produce more accurate reconstructions with higher image quality parameters as resolution, contrast, and or signal to noise ratio. Alternatively, the number of projections acquired can be reduced to lower the dose. Since the method in general produces more accurate reconstructions, it has been shown experimentally that a reconstruction of a given quality can be produced with a reduced number of projections. In addition, since in several modalities including that of the current example, the scan acquisition time is proportional to the number of projections, the acquisition time is reduced since fewer projections are acquired. Furthermore, since higher signal to noise ratios can be produced by this method, it is possible to lower the dose by decreasing the radiation flux of each projection. Consequently, a reconstruction of a given quality can be produced with a lower dose to the subject.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In any appended claims, reference to an element in the singular is not intended to mean "one and only one" unless explicitly so stated, but rather "one or more." All structural, chemical, and functional equivalents to the elements of the above-described preferred embodiments that are known to those of ordinary skill in the art are expressly incorporated herein by reference and are intended to be encompassed by the present disclosure. Moreover, it is not necessary for a device or method to address each and every problem sought to be solved by the present invention, for it to be encompassed by the present disclosure. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for reconstructing an image representation of an object from its projections, comprising:
   obtaining projection data from an imager; and
   processing said projection data with a computer, comprising:
      mapping Fourier transformed projection data in Fourier space;
      converting iteratively said projection data from Fourier space to object space;
      refining said projection data;
      modifying said refined projection data in Fourier space and in object space to produce progressively modified projection data; and
      generating an image from said modified projection data.

2. A method as recited in claim 1, further comprising refining said projection data in Fourier space and refining said projection in object space with each iteration.

3. A method as recited in claim 2, wherein said refinement is a mathematical transformation selected from the group of transformations consisting essentially of: a denoising transformation, a deconvolution transformation, a deblurring transformation, an image restoration transformation, and a filtering transformation.

4. A method as recited in claim 3, wherein said mathematical transformation is a transformation selected from the group of transformations comprising essentially of: a Wiener filtering/deconvolution, a Rudin-Osher-Fatemi (ROF) total variation (TV) algorithm, a Nonlocal means algorithms, a Penalized likelihood method, a Kalman filtering/deconvolution and its variants, a Speckle filter, a Simple filters such as Gaussian filters, Laplacian filters, low pass filters, high pass filters, edge enhancing filters (such as Prewitt, Sobel), an Anisotropic filter, a Deconvolution algorithms based on a known or user defined point spread function, Wavelet denoising, Neighborhood filters, a SUSAN filter, a Discrete universal denoiser and an unsupervised information-theoretic, adaptive filter.

5. A method as recited in claim 1, further comprising mathematically transforming said projection data prior to mapping said obtained projection data.

6. A method as recited in claim 5, wherein said mathematical transformation is a transformation selected from the group of transformations consisting essentially of: a denoising transformation, a deconvolution transformation, a deblurring transformation, an image restoration transformation, and a filtering transformation.

7. A method as recited in claim 1, wherein said processing of said projection data further comprises:
   creating a scanner profile of said imager with a scanner imaging field;
   determining expected voxel values of said imaging field;
   scanning a specimen with said scanner; and reconstructing an image of the specimen from the scan utilizing said scanner profile and the expected voxel values of the imaging field and any objects of interest within the imaging field surrounding said specimen in the reconstruction process.

8. A method for reconstructing an image of an object from its projections, comprising:
   obtaining projection data;
   generating a Fourier transform of the projections at a plurality of angles and slice locations;
   placing the transformed projections onto a grid in Fourier space;
   performing an initializing modification of Fourier space;
   performing an inverse transformation of said Fourier space data to provide an object space image;
   refining said object space image;
   modifying said refined object space image to produce a modified object space image;
   performing a forward Fourier transformation on said modified object space image to produce Fourier space data;
   refining said Fourier space data to product refined Fourier space data;
   modifying said refined Fourier space data to produce a modified Fourier space data; and
   applying said inverse Fourier transformation, refinement, modification, forward Fourier transformation, refinement and modification steps iteratively to the said modified Fourier space data until a termination condition is satisfied to provide a final image.

9. A method as recited in claim 8, further comprising mathematically transforming said transformed projections prior to initial modification.

10. A method as recited in claim 9, wherein said mathematical transformation is a transformation selected from the group of transformations comprising essentially of: a denoising transformation, a deconvolution transformation, a deblurring transformation, an image restoration transformation, and a filtering transformation.

11. A method as recited in claim 10, wherein said mathematical transformation is a transformation selected from the group of transformations consisting essentially of: a Wiener filtering/deconvolution, a Rudin-Osher-Fatemi (ROF) total variation (TV) algorithm, a Nonlocal means algorithms, a Penalized likelihood method, a Kalman filtering/deconvolution and its variants, a Speckle filter, a Simple filters such as Gaussian filters, Laplacian filters, low pass filters, high pass filters, edge enhancing filters (such as Prewitt, Sobel), an Anisotropic filter, a Deconvolution algorithms based on a known or user defined point spread function, Wavelet denoising, Neighborhood filters, a SUSAN filter, a Discrete universal denoiser and an unsupervised information-theoretic, adaptive filter.

12. A method as recited in claim 8, further comprising:
   applying a first refinement of said object space data during a first iteration between object space and Fourier space; and
   applying a second refinement of said object space data during a second iteration between object space and Fourier space.

13. A method as recited in claim 8, wherein said first refinement is a denoising transformation and said second refinement is a deconvolution transformation.

14. A method as recited in claim 12, further comprising:
   applying a first refinement of said Fourier space data during a first iteration between Fourier space and object space; and
   applying a second refinement of said Fourier space data during a second iteration between Fourier space object space.

15. A method as recited in claim 8, wherein said refining steps are applied to said projection data every other iteration.

16. A method for tomographic imaging, comprising:
   obtaining equally sloped projection data from an imager;
   denoising said projection data;
   padding projection data with zeros with a suitable amount of zeros;
   generating a one dimensional Fractional Fast Fourier transform of the projections at a plurality of angles and slice locations;
   placing the transformed projections onto a pseudopolar grid in Fourier space;
   storing locations and values of said Fourier transformed projections;
   performing a inverse two dimensional Pseudopolar Fast Fourier Transform of each 2D slice in Fourier space to provide object space data;
   refining said object space data to produce refined object space data;
   modifying said refined object space data to produce a modified object space data;
   performing a forward two dimensional Pseudopolar Fast Fourier Transform of each 2D slice of object space data to produce Fourier space data;
   modifying said Fourier space data to produce a modified Fourier space data; and
   applying said inverse Fourier transformation, modification, forward Fourier transformation and modification steps iteratively to the said modified Fourier space data until a termination condition is satisfied to provide a final image.

17. A method as recited in claim 16, further comprising refining said Fourier space data prior to modification.

18. A method as recited in claim 17, wherein said refining comprises a mathematical transformation selected from the group of transformations consisting essentially of: a denoising transformation, a deconvolution transformation, a deblurring transformation, an image restoration transformation, and a filtering transformation.

19. A non-transitory computer-readable storage medium having computer-readable program code portions stored therein and providing for associative relevancy knowledge profiling, which when executed on a computer the computer-readable program code portions perform steps comprising:
   a first program code configured for obtaining projection data;
   a second program code configured for mapping Fourier transformed projection data in Fourier space;
   a third program code configured for converting iteratively the projection data from Fourier space to object space;
   a fourth program code configure for refining said projection data;
   a fifth program code configured for modifying said projection data in Fourier space and in object space to produce progressively modified projection data; and
   a sixth program code configured for generating an image from said modified projection data.

20. A non-transitory computer readable storage medium as recited in claim 19, said steps further comprising:
   a sixth program code configured to mathematically transform said projection data prior to mapping.

* * * * *